(12) United States Patent
Blanchard (10) Patent No.: US 9,114,227 B2
(45) Date of Patent: Aug. 25, 2015

(54) SHIELDING DILATOR FOR USE WITH A CATHETER

(75) Inventor: Daniel B. Blanchard, Bountiful, UT (US)

(73) Assignee: C. R. Bard, Inc., Murray Hill, NJ (US)

(*) Notice: Subject to any disclaimer, the term of this patent is extended or adjusted under 35 U.S.C. 154(b) by 136 days.

(21) Appl. No.: 13/344,945

(22) Filed: Jan. 6, 2012

(65) Prior Publication Data

US 2012/0179102 A1 Jul. 12, 2012

Related U.S. Application Data

(60) Provisional application No. 61/430,674, filed on Jan. 7, 2011.

(51) Int. Cl.
| | |
|---|---|
| *A61M 29/00* | (2006.01) |
| *A61B 17/34* | (2006.01) |
| *A61M 25/00* | (2006.01) |
| *A61M 25/01* | (2006.01) |
| *A61M 29/02* | (2006.01) |

(52) U.S. Cl.
CPC ............ *A61M 29/00* (2013.01); *A61B 17/3415* (2013.01); *A61M 25/0023* (2013.01); *A61M 25/0069* (2013.01); *A61M 25/0082* (2013.01); *A61M 25/0009* (2013.01); *A61M 25/01* (2013.01); *A61M 29/02* (2013.01); *A61M 2025/0024* (2013.01)

(58) Field of Classification Search
CPC ......................... A61M 29/02; A61M 2029/025
USPC ............ 604/164.1, 164.11, 528, 913, 164.01, 604/164.03
See application file for complete search history.

(56) References Cited

U.S. PATENT DOCUMENTS

| | | | | | |
|---|---|---|---|---|---|
| 3,822,238 | A | * | 7/1974 | Blair et al. ...................... | 528/59 |
| 3,975,350 | A | * | 8/1976 | Hudgin et al. ................. | 524/108 |
| 4,156,066 | A | * | 5/1979 | Gould ......................... | 424/78.06 |
| 4,255,550 | A | * | 3/1981 | Gould ............................. | 528/44 |
| 4,408,023 | A | * | 10/1983 | Gould et al. ................. | 525/454 |
| 4,424,305 | A | * | 1/1984 | Gould et al. .................. | 514/557 |
| 4,439,554 | A | * | 3/1984 | Argentar ....................... | 523/115 |
| 4,439,558 | A | * | 3/1984 | Tamosauskas et al. ........ | 523/217 |
| 4,439,583 | A | * | 3/1984 | Gould et al. .................. | 525/127 |

(Continued)

FOREIGN PATENT DOCUMENTS

WO 2012094583 A2 7/2012

OTHER PUBLICATIONS

PCT/US2012/020465 filed Jan. 6, 2012 International Search Report and Written Opinion dated Apr. 25, 2012.

*Primary Examiner* — Aarti B Berdichevsky
(74) *Attorney, Agent, or Firm* — Rutan & Tucker, LLP (57) ABSTRACT

A dilator system for insertion of a catheter or other elongate device into a body of a patient includes a catheter having a lumen that initially defines a first inner diameter. The catheter includes a swellable material that swells after insertion into the body. A dilator includes an elongate body that is initially disposed in the catheter lumen and a tapered head extending from a distal end of the catheter lumen. The dilator head defines an outer diameter that is larger than the first inner diameter of the catheter lumen. After insertion of the dilator head and a distal portion of the catheter into the body, the catheter swells such that the lumen defines a second inner diameter that is larger than the outer diameter of the dilator head. This enables the dilator to be proximally removed from the body via the catheter lumen defining the second diameter.

16 Claims, 10 Drawing Sheets

(56) References Cited

U.S. PATENT DOCUMENTS

| | | | |
|---|---|---|---|
| 4,610,671 A * | 9/1986 | Luther | 604/168 |
| 4,710,181 A | 12/1987 | Fuqua | |
| 4,883,699 A | 11/1989 | Aniuk et al. | |
| 5,456,713 A * | 10/1995 | Chuter | 623/1.23 |
| 5,755,777 A * | 5/1998 | Chuter | 623/1.11 |
| 6,436,119 B1 | 8/2002 | Erb et al. | |
| 2002/0022046 A1 | 2/2002 | Tedeschi et al. | |
| 2006/0212022 A1 | 9/2006 | Gellman | |

* cited by examiner

SHIELDING DILATOR FOR USE WITH A CATHETER

CROSS-REFERENCE TO RELATED APPLICATIONS

This application claims the benefit of U.S. Provisional Patent Application No. 61/430,674, filed Jan. 7, 2011, and titled "Shielding Dilator for Use With a Catheter," which is incorporated herein by reference in its entirety.

BRIEF SUMMARY

Briefly summarized, embodiments of the present invention are directed to catheter assemblies and particularly dilators for use in providing access for a catheter, introducer, or other tubular medical device/component to an interior portion of a patient via an insertion site.

In one embodiment, a dilator system for insertion of a catheter into a body of a patient comprises a catheter including a lumen that initially defines a first inner diameter. The catheter includes a swellable material that swells after insertion into the body. A dilator is also disclosed and includes an elongate body that is initially disposed in the catheter lumen and a tapered head extending from a distal end of the catheter lumen. The dilator head defines an outer diameter that is larger than the first inner diameter of the catheter lumen. After insertion of the dilator head and a distal portion of the catheter into the body, the catheter swells such that the lumen defines a second inner diameter that is larger than the outer diameter of the dilator head. This enables the dilator to be proximally removed from the body via the catheter lumen defining the second diameter.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present disclosure are generally directed to catheter assemblies and particularly dilators for use in providing access for a catheter, introducer, or other elongate or tubular medical device/component to an interior portion of a patient via an insertion site. As will be seen, the catheter assemblies and dilators to be shown and described herein are configured to be modified in size, shape, and/or appearance so as to facilitate ease of catheter insertion.

Reference is first made to FIGS. 1A-2B, which depict a dilator, generally designated at 20, for assisting with the insertion of a tubular device, such as a catheter, into the body of a patient according to one embodiment. An example of a catheter 12 with which the dilator 20 can be employed is cross sectionally shown in FIG. 2B. The catheter 12 includes an elongate body extending between a proximal end and a distal end 12B and further defines one or more lumens 14. Though a catheter is described herein, it should be remembered that the dilators to be discussed can be employed with other tubular devices, including introducers, for example. In addition, the dilators can be used to place catheters and other elongate/tubular devices into a vessel or other internal body portion, including placement of a feeding tube into the digestive tract, a drainage catheter into a body cavity to be drained, etc.

Figure 1A:
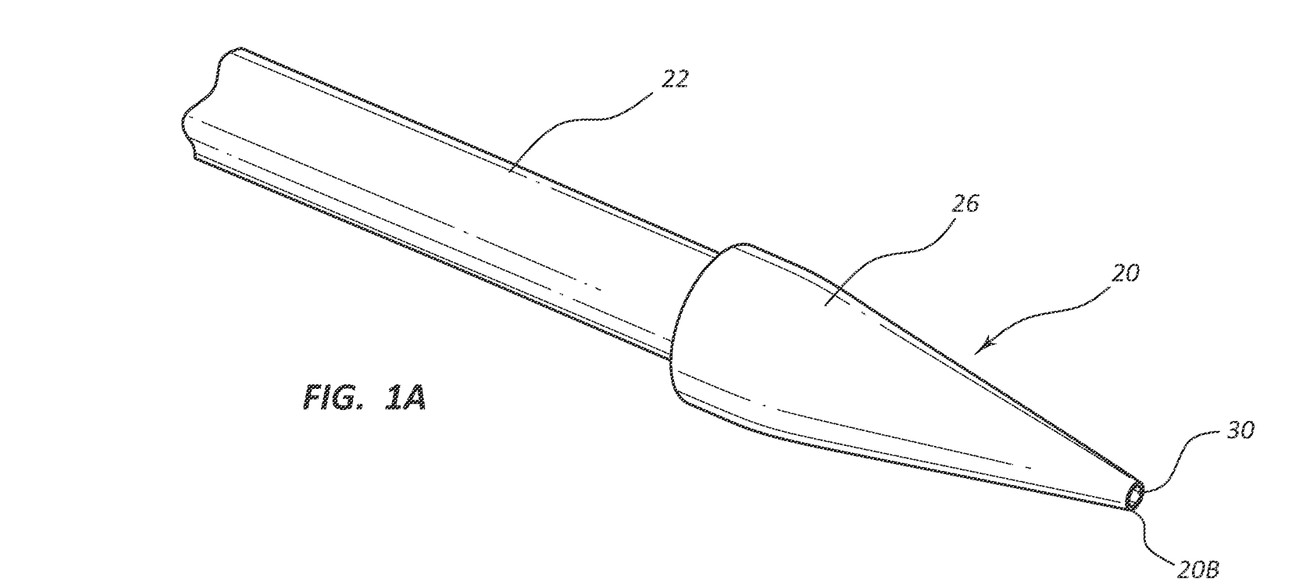
FIGS. 1A and 1B are various views of a dilator according to one embodiment.
Figure 1B:
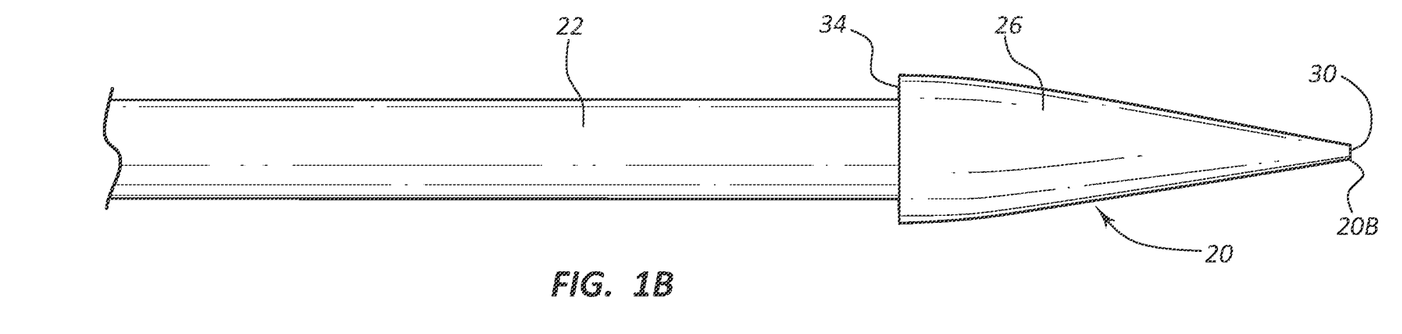

FIGS. 1A and 1B show that the dilator 20 includes an elongate dilator body 22 configured for insertion into the lumen 14 of the catheter. A distal head 26 is included with the dilator body 22 so as to define a distal end 20B of the dilator 20. Note that the distal head 26 can be formed integrally with or attachably separate from the dilator body 22, and that the dilator can include a metal, a plastic, or other suitable, sufficiently rigid material to enable the dilator to widen an incision/insertion site through which the catheter must pass to gain access to an internal portion of the body of a patient, such as a subcutaneous vessel, for instance. In the present embodiment, the distal head 26 defines a generally conical shape so as to be able to suitably dilate the insertion site. Other head shapes are also possible.

Figure 2A:
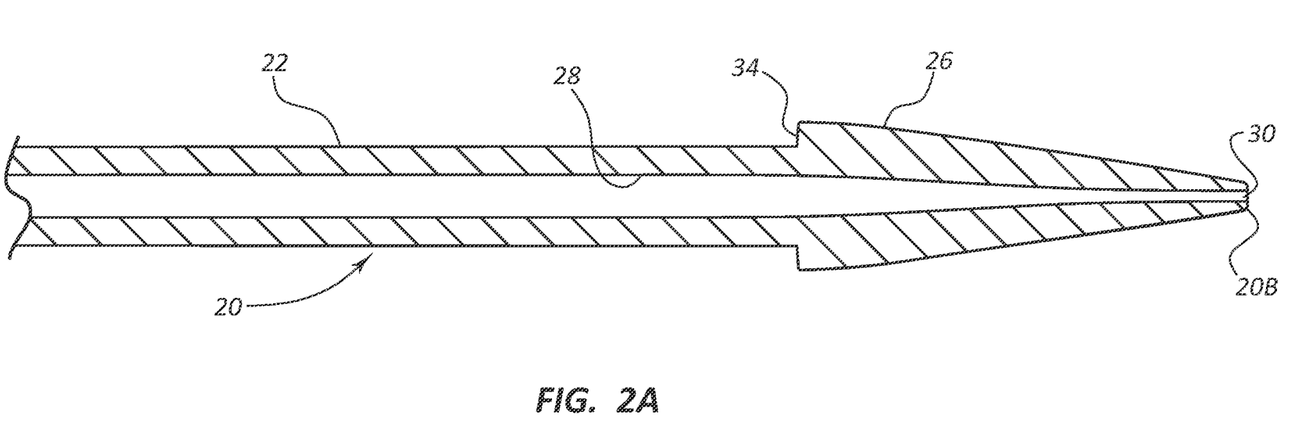
FIGS. 2A and 2B are cross sectional side views of the dilator of FIG. 1 both by itself (FIG. 2A) and inserted into a catheter (FIG. 2B)

As seen in FIG. 2A, the dilator 20 defines a guidewire channel 28 for receiving therethrough a guidewire, often used for placing a catheter within a vasculature of the patient. The guidewire channel 28 terminates distally at a distal opening 30 at the distal end 20B of the dilator 20. In addition, a needle could be passed through the channel 28, in one embodiment.

Figure 2B:
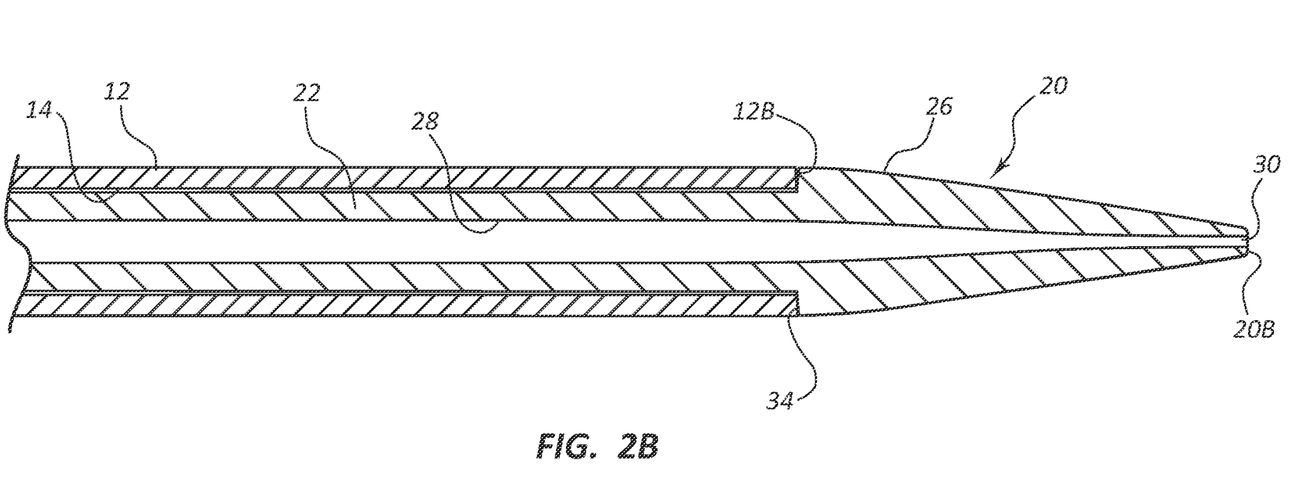

As shown in FIG. 2B, the dilator 20 is shown mated with the catheter 12, wherein the elongate dilator body 22 is sized so as to be received within the catheter lumen 14 and the dilator head 26 extends past the catheter distal end 12B. The catheter distal end 12B is positioned so as to abut and be substantially adjacent to a shoulder 34 defined between the dilator body 22 and head 26. Note that the catheter lumen 14 defines an inner diameter, as seen in FIG. 2B.

The distal head 26 of the dilator 20 is tapered and sized so as to enlarge the insertion site. Further, a proximal portion of the dilator head 26 defines an outer diameter so as to provide a "shadow" for the distal portion of the catheter 12 as the catheter is passed through the insertion site and into a vessel or other body portion so that the catheter is inserted into the patient body without substantial resistance.

Figure 3A:
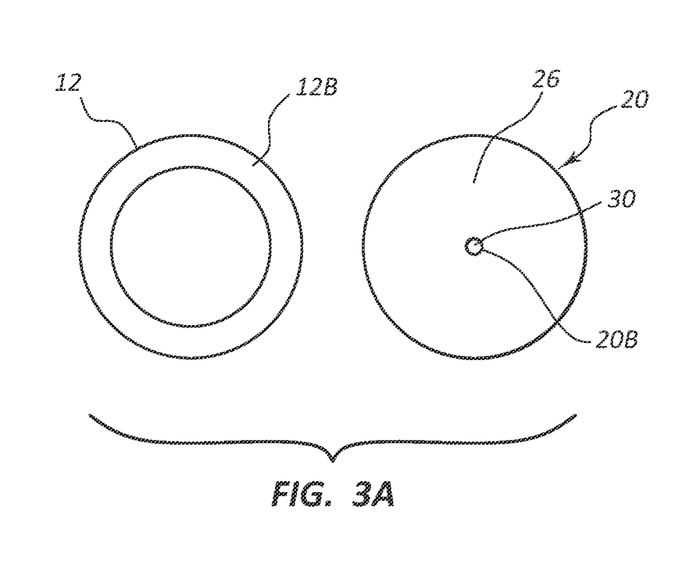
FIGS. 3A and 3B show distal end views of the catheter and dilator of FIG. 2B in a first and a second state, respectively.
Figure 3B:
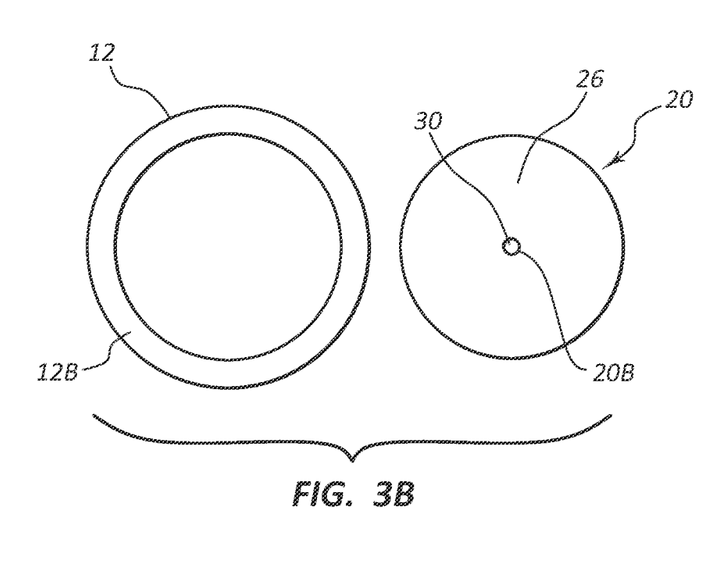

During use, once the distal portion of the catheter 12 has been suitably positioned within the patient body, it is necessary to remove the dilator 20. In the present embodiment, the catheter 12 includes a hydrating or swellable material that, when hydrated by body fluids, water, etc. or otherwise swelled, causes the catheter lumen 14 to swell in diameter to a second, larger inner diameter. An example of this is depicted in FIGS. 3A and 3B, where distal end views of the dilator 20 and the catheter 12 both prior to (FIG. 3A) and after (FIG. 3B) catheter hydration are shown. As illustrated in FIG. 3A, before hydration the inner diameter of the catheter lumen 14 is relatively small so that the catheter 12 resides within the shadow of the proximal portion of the dilator head 26. After hydration, in contrast, the catheter 12 swells such that the lumen 14 thereof defines a second, larger inner diameter that is greater than the outer diameter of the dilator head 26. Again, such catheter hydration can occur, for instance, when the catheter is disposed in the bloodstream within the patient's vasculature. In one embodiment, slits or slots in the wall of the dilator are defined to enable hydration of portions of the catheter that reside outside of the patient's vasculature.

Once such an increase in the inner diameter of the catheter lumen 14 occurs, the dilator can be slid proximally through the swelled catheter 12 and removed from the body. One example of a hydrating material from which the catheter 12 can be formed includes a composite hydrogel including chemically enhanced polyurethane and polyethylene oxide known by the trademark AQUAVENE®. Other hydratable materials can also be employed, such as plastics including a hydrophilic and/or water-absorbing component. For instance, a polymer including polyethylene glycol ("PEG") in the polymer chain or compounded therewith can be used. In other embodiment, heat-activated swelling materials can be employed.

One benefit of the above and other configurations described herein is the ability to employ relatively softer materials for the catheter body than what would otherwise be possible. For instance, the present configurations can enable a relatively soft, atraumatic distal tip to be included on the catheter. As mentioned, note that an introducer can be substituted for the catheter described herein. As such, the principles of the present embodiments are not limited to catheters.

Figure 4A:
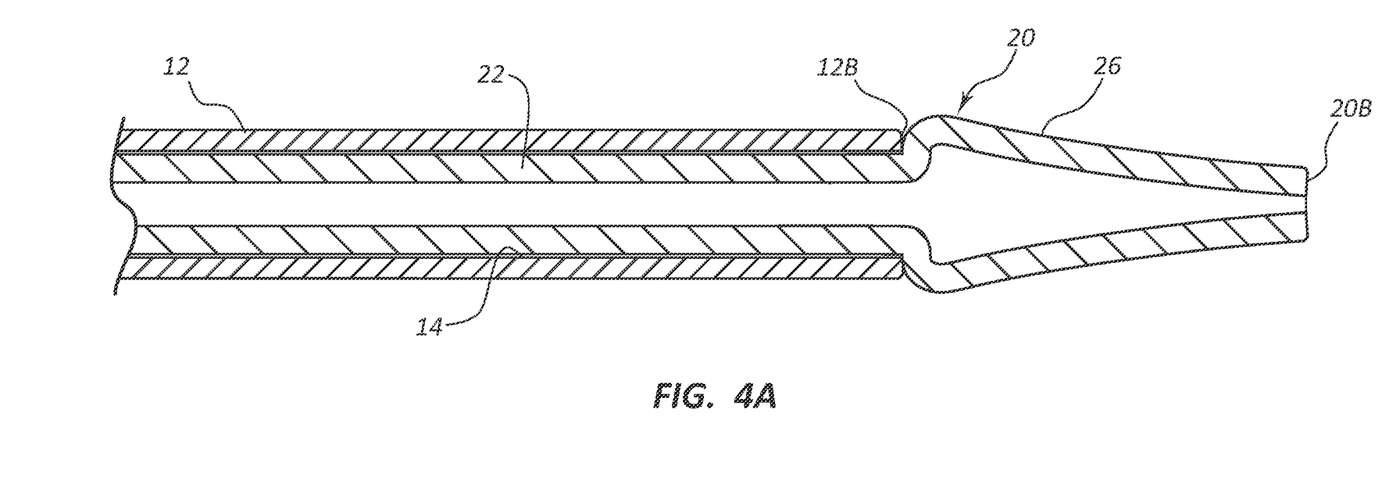
FIGS. 4A and 4B show cross sectional views of a catheter assembly including a dilator according to one embodiment.
Figure 4B:
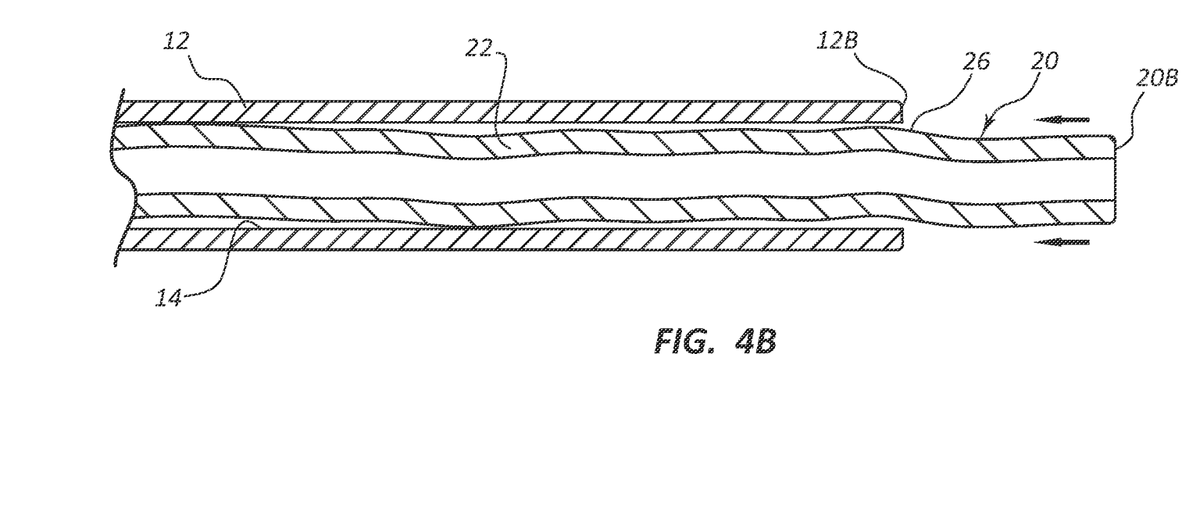

FIGS. 4A and 4B show a dilator configuration according to another embodiment, wherein the body 22 and distal head 26 of the dilator 20 includes a hydrating material, similar to the catheter of the previous embodiment. So configured, the dilator head 26 can be initially formed in a sufficiently hard tapered shape with a suitably large outer diameter to ease passage of the dilator and attached catheter 12 through an insertion site. Then, upon insertion into the patient's body, the dilator head 26 is hydrated, such as by water, blood, and/or body fluids upon insertion into the patient's body. This causes the dilator head 26 soften so as to enable the head to deform and the dilator 20 to be pulled proximally from the catheter 12 and removed via the lumen 14 thereof, as shown in FIG. 4B. The dilator 20 can be formed via extrusion, overmolding, and/or RF tipping to define the dilator head 26.

Note that in the present embodiment the walls of the dilator 20 are relatively thin to hasten the softening process. Note also that, though shown in FIGS. 4A and 4B as being integral to one another, in one embodiment it is appreciated that the distal head can be separately formed from the dilator body, and that the distal head can include the hydrating material while the dilator body does not. In another embodiment, the dilator can include a temperature-dependent softening material that remains sufficiently stiff at room temperature, but softens at body temperature. These and other possible variations are therefore contemplated.

Figure 5:
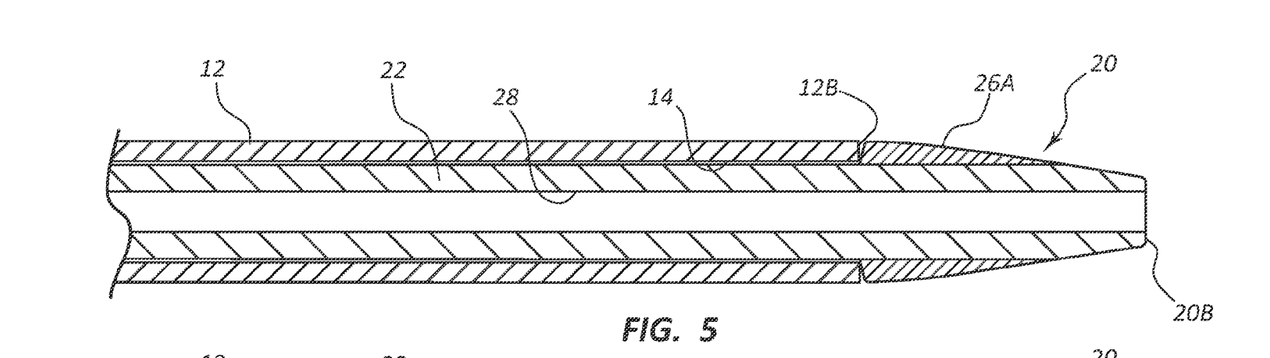
FIG. 5 is a cross sectional view of a catheter assembly including a dilator according to one embodiment.

FIG. 5 shows a dilator configuration according to another embodiment, wherein the dilator 20 includes the body 22 thereof extending to the distal end 20B thereof. The distal head 26 defining a sufficiently large outer diameter is included on the dilator 20, as before, to define a shadow for easing passage of the catheter 12 through the insertion site, but further includes in the present embodiment an external portion 26A that defines the conically tapered outer surface thereof. The external portion 26A includes a bioresorbable material, which dissolves in and is absorbed by body fluids, such as water and blood, when the dilator is inserted into a vessel of the patient.

So configured, the dilator 20 of FIG. 5 can be used to enlarge an insertion site into the patient's vasculature (or other internal body portion) so as to ease insertion of the dilator and catheter 12 into the bloodstream of the vessel. Once positioned in the bloodstream, the external portion 26A of the dilator head 26 readily dissolves in the blood stream, which reduces the outer diameter of the distal head to that of the dilator body 22. The dilator 20 can then be easily removed proximally through the inner diameter of the lumen 14 of the catheter 12. Note that in one embodiment the external portion of the dilator head can include a dissolving material, including ABSORV™ bioabsorbable polymers by Zeus, Inc. of Orangeburg, S.C., polysaccharides, bioresorbable materials under the TRANCERTA™ drug delivery portfolio by DSM Biomedical of Berkeley, Calif., etc. In other embodiments, more or less than the external portion 26A shown in FIG. 5 can include the bioresorbable material. In yet another embodiment, antihistamine can be added to the bioresorbable material to alleviate the effects of damage or trauma to the vessel into which the catheter is inserted. In other embodiments the external portion 26A can include other materials that dissolve or otherwise disappear upon insertion into the body, including water ice or other iced materials, dissolvable food-based products, sugar, materials that change from solid to liquid or gas state upon insertion into the body, etc.

Figure 6:
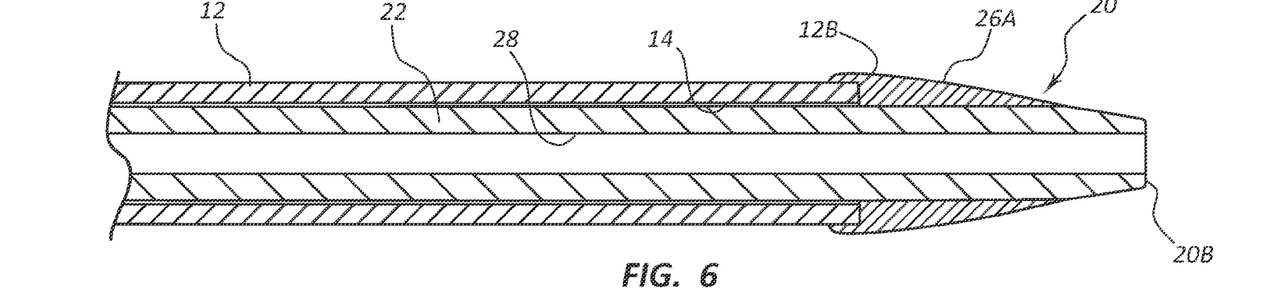
FIG. 6 is a cross sectional view of a catheter assembly including a dilator according to one embodiment.

FIG. 6 shows one possible variation of the dilator 20 of FIG. 5, wherein the external portion 26A of the distal head 26 extends proximally to cover the distal end 12B of the catheter 12. This configuration prevents rollback or peeling of the catheter distal end 12B, and further provides a smooth transition between the dilator 20 and the catheter 12 during catheter insertion. After the external portion 26A is dissolved in the bloodstream, the dilator is easily removed from the catheter, as before.

Figure 7:
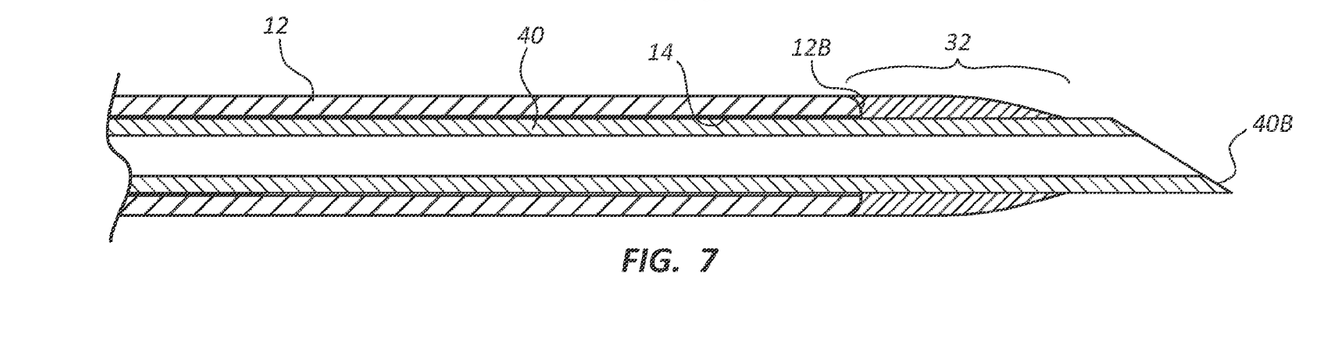
FIG. 7 is a cross sectional view of a catheter assembly including a needle according to one embodiment.

FIG. 7 shows that the above principles can be applied to other insertion configurations, such as an IV needle and catheter assembly as depicted in FIG. 7. Specifically, FIG. 7 shows that in one embodiment a distal portion 32 of the catheter 12 includes a bioresorbable material that is relatively stiffer than more proximal portions of the catheter. In addition, the distal edge of the distal portion 32 is angled so as to provide a smooth transition between the bevel of a needle 40 that is disposed within the lumen of the catheter 12. The shape and relative stiffness of the distal portion 32 enables the catheter 12 and the needle 40 to readily pass through an insertion site and into the patient's vasculature. Once positioned in the vessel bloodstream, the bioresorbable distal portion 32 dissolves, the needle 40 is removed, and an atraumatic, soft distal catheter end 12B remains in the vasculature. Note that similar principles can be applied to other catheters and devices for transcutaneous insertion.

Figure 8A:
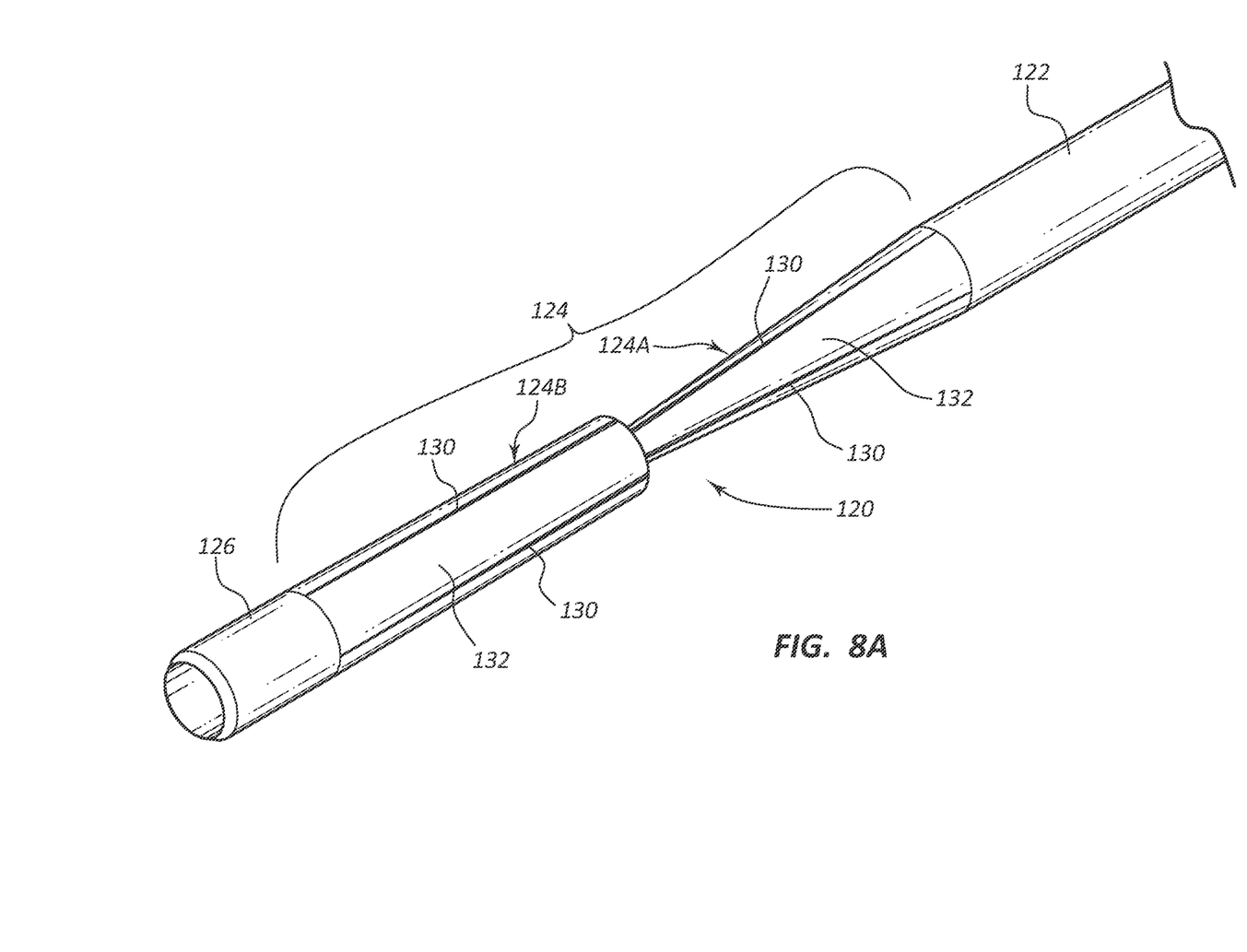
FIGS. 8A-8C show various views of a dilator according to one embodiment.
Figure 8B:
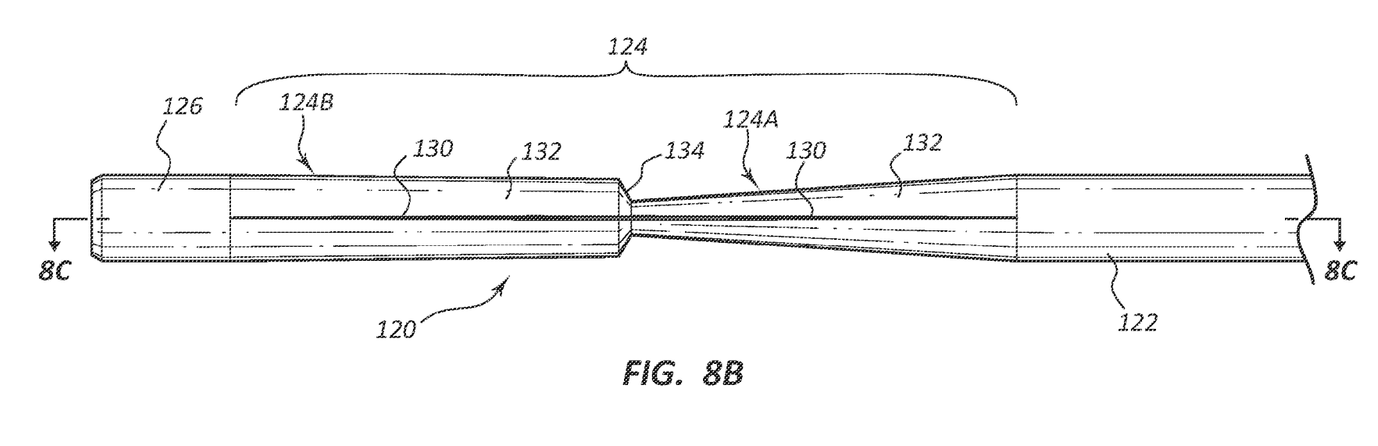
Figure 8C:
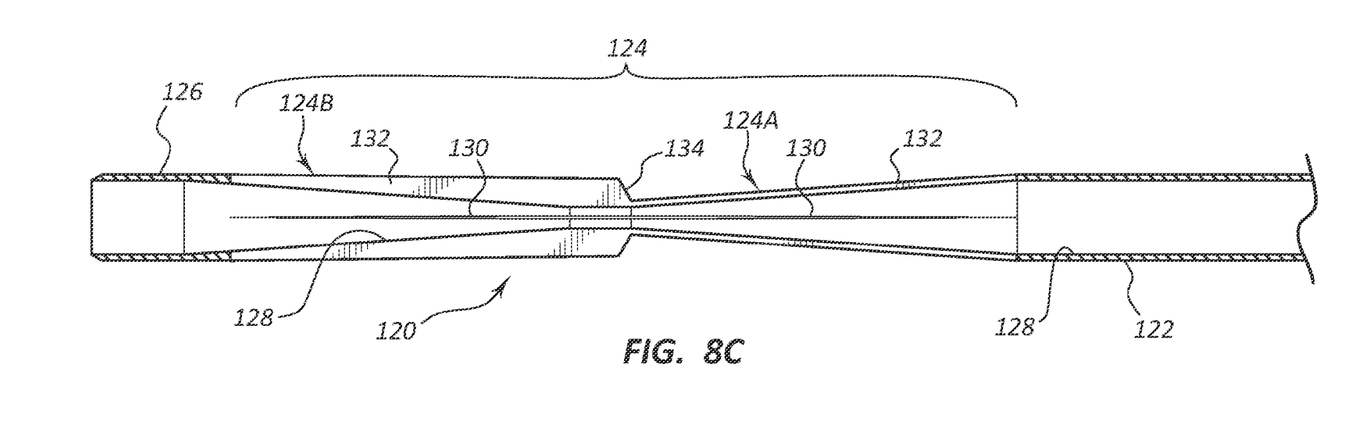

FIGS. 8A-8C depict details of a dilator 120 configured according to another embodiment, wherein the dilator includes an elongate body 122 that defines an expansion portion 124. The expansion portion 124 in turn defines a proximal segment that defines a distally converging conical shape, and an initially cylindrical distal segment. A distal end portion 126 is disposed distal to the distal segment of the expansion portion and defines the tip of the dilator 120.

A plurality of slits 130 is included on the expansion portion 124, each extending through the dilator wall from an external dilator surface to a lumen 128 of the dilator body 122. The slits 130 help define each of a plurality of separate dilating segments 132 that span the length of the expansion portion 124, similar to a collet. The dilating segments 132 are separately expandable from one another and are each attached to adjacent portions of the dilator body 122 at either end. In the present embodiment, four slits to define four dilating segments are included. Other numbers, sizes, and shapes of slits and segments can be employed. Generally, at least three slits are desired.

Figure 9:
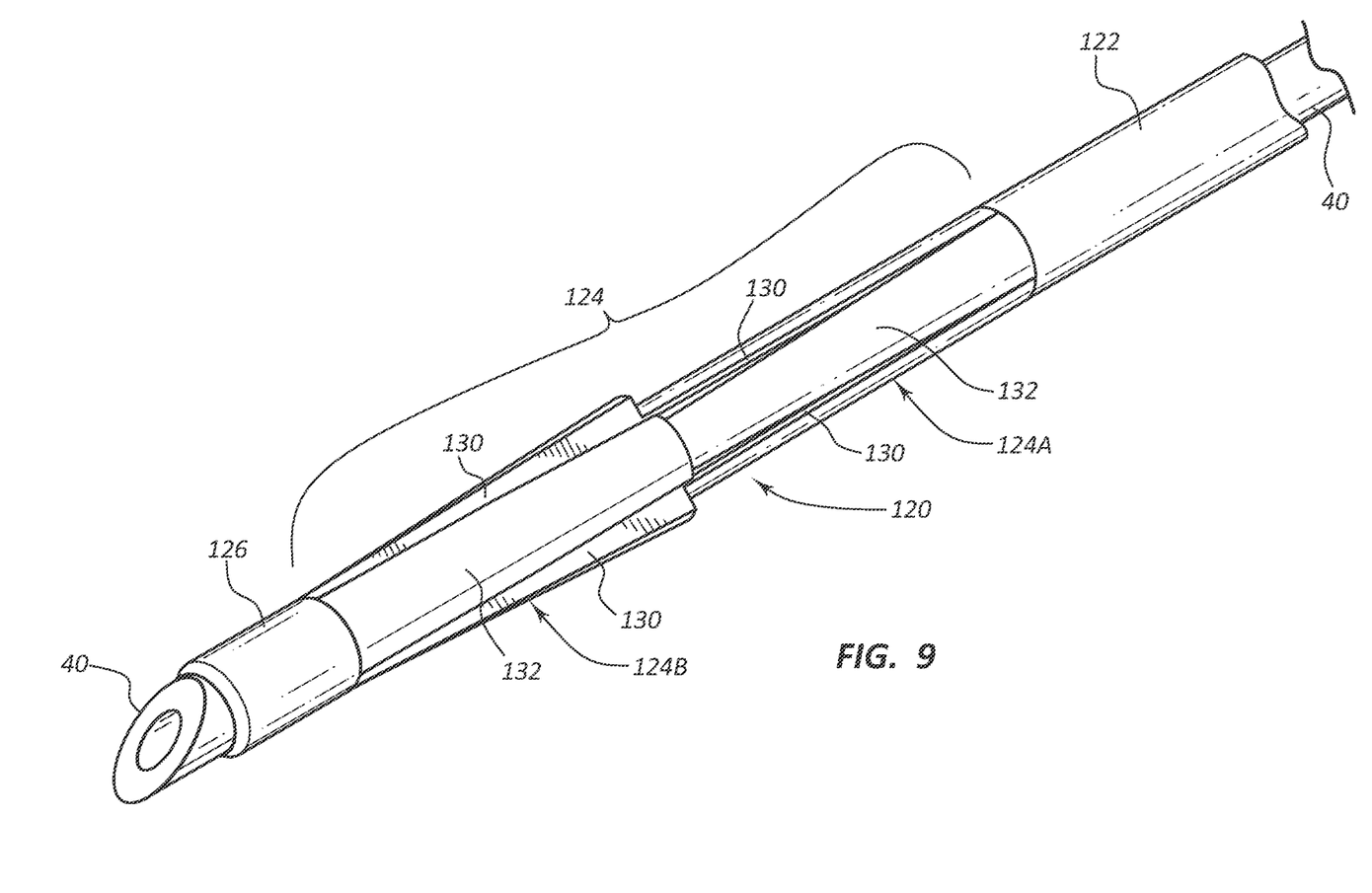
FIG. 9 is a perspective view of the dilator of FIGS. 8A-8C in a dilating state.
Figure 10A:
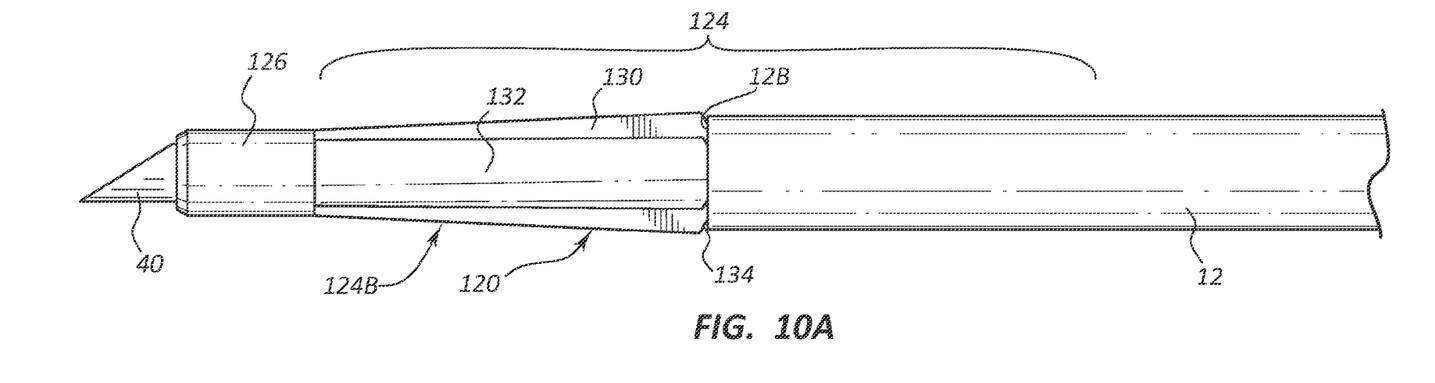
FIGS. 10A and 10B are side and cross sectional side views, respectively, of the dilator of FIGS. 8A-8C in a dilating state and received within a catheter.
Figure 10B:
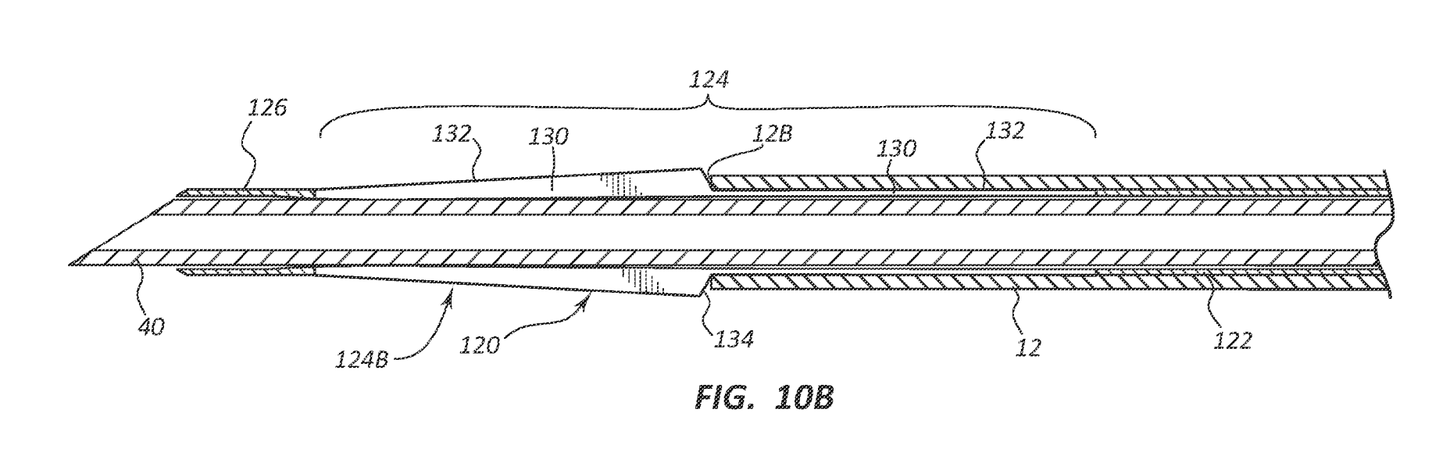

The dilating segments 132 are radially expandable when a needle 40 or other elongate element such as a guidewire is inserted through the dilator lumen 128 distally past the expansion portion 124, as best seen in FIGS. 9-10B. Note that the lumen 128 converges to a relatively small diameter in the proximal segment of the expansion portion 124, a diameter that is smaller relative to the outer diameter of the needle 40 that is to pass therethrough. Thus, when the needle 40 is passed through the reduced diameter section of the lumen 128, the dilating segments 132 are pushed radially outward to increase the size of the lumen and allow the needle to pass through the lumen.

The above radial expansion of the dilating segments 130 causes the distal portion of the dilating segments to define a generally conically tapered dilator head that in turn substantially defines a maximum outer diameter. This provides a shadow for the catheter 12 that is slid on to the dilator 120 as shown in FIGS. 10A and 10B. As shown, the distal portions of the dilating segments 132 define a shoulder 134 against which the distal end 12B of the catheter 12 can rest during insertion of the mated dilator and catheter past an insertion site in the patient's body. Note that the needle 40 cooperates with the distal end of the dilator distal portion 126 and the dilating segments to provide suitable penetration and dilation for advancement of the catheter into the vessel of other internal body portion.

Once placement of the catheter 12 within the vessel is complete, the needle 40 can be withdrawn from the dilator lumen 128, which enables the dilating segments to radially collapse to their initial state shown in FIGS. 8A-8C. In this collapsed state, the dilator 120 can be readily withdrawn from the catheter 12 via the lumen 14 thereof, leaving the catheter in place. As mentioned. note that the number, size, and shape of the dilating segments of the present dilator can vary from what is shown and described.

In one embodiment, the dilator 120 is manufactured by molding or extruding the dilator body 122, then adding the distal portion 126 by overmolding or RF tipping. The expansion portion 124 is then cut longitudinally to define the various slits 130 and dilating segments 132. Other manufacturing processes are, of course, contemplated. In one embodiment, suitable materials from which the dilator can be manufactured include polyethylene, polypropylene, isoplast, synthetic polymer polyamides, acetyl resin, and other medical polymers.

Figure 11A:
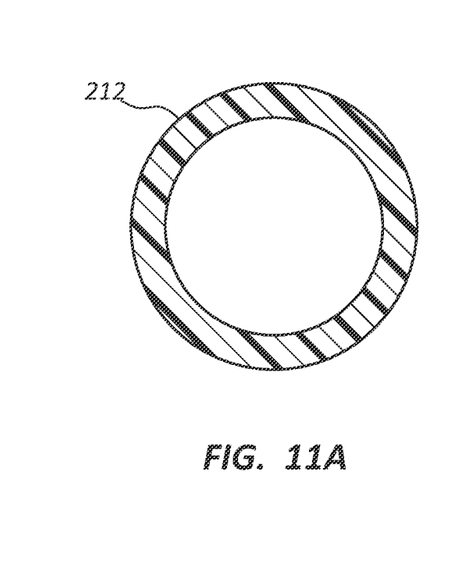
FIGS. 11A-11D show cross sectional views of a catheter configured according to one embodiment.
Figure 11B:
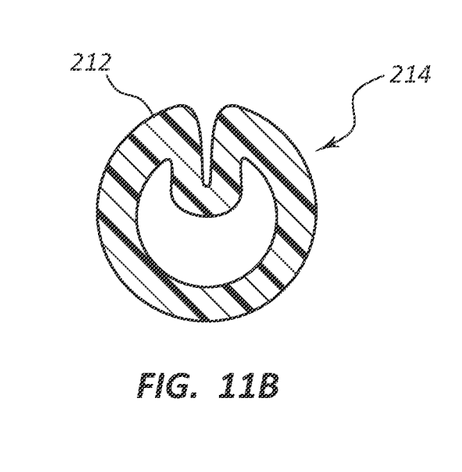
Figure 11C:
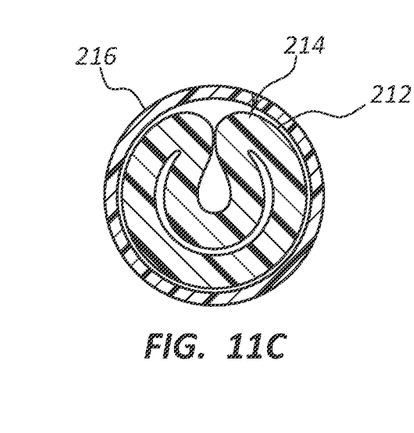
Figure 11D:
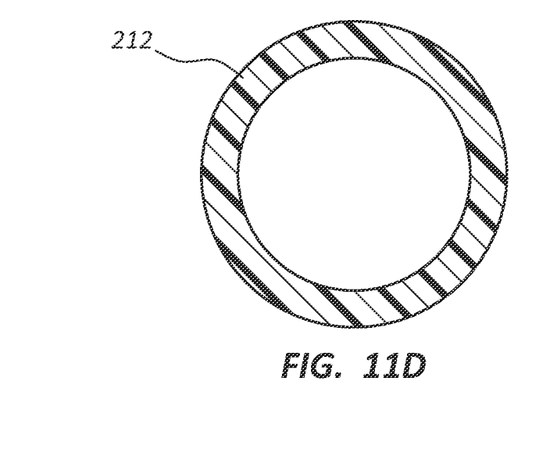

FIGS. 11A-11D depict various details regarding a catheter 212 configured in accordance with one embodiment, wherein the body of the catheter is foldable, after formation by extrusion or other suitable process. In particular, FIG. 11A cross sectionally shows the catheter after formation by extrusion, while FIG. 11B shows the catheter subsequently folded along its longitudinal length in C-shaped configuration 214, though other folded configurations are also possible. As shown in FIG. 11C, the catheter 212, while in the folded configuration 214 can be placed in an introducer, cross sectionally shown at 216, that defines a diameter sufficient only for the catheter in the folded configuration. The catheter 212 is inserted into the vasculature via the introducer while still in the folded configuration 214. As shown in FIG. 11D, after insertion, the introducer is removed from the patient's body and the catheter 212 is flushed to cause the catheter to unfold into its original unfolded state, ready for use. Suitable materials from which the catheter can be manufactured include, for instance, silicone of about 40-70 durometer, and other materials.

In one embodiment, the catheter 212 can include a swellable material as described in previous embodiments. In this case, the catheter is hydrated by its placement in the vasculature while still in the folded configuration. Catheter hydration will cause the catheter to unfold and resume its round cross sectional shape. Note that various folded configurations can be used, depending on the relative size of the catheter and the introducer into which the folded catheter is placed during insertion.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A dilator system for insertion of an elongate device into a body of a patient, comprising:
    an elongate device including a lumen initially defining a first inner diameter, the elongate device including a swellable material that swells after insertion into the body; and
    a dilator including an elongate body initially disposed in the elongate device lumen and a tapered head extending from a distal end of the elongate device lumen, the dilator head defining an outer diameter substantially equal to or larger than the first inner diameter of the elongate device lumen, the dilator defining a guidewire lumen for passage therethrough of a guidewire, wherein after insertion of the dilator head and a distal portion of the elongate device into the body at least the distal portion of the elongate device swells such that the lumen defines a second inner diameter larger than the outer diameter of the dilator head that enables the dilator to be proximally removed from the body via the elongate device lumen defining the second diameter.

2. The dilator system as defined in claim 1, wherein the elongate device is a catheter.

3. The dilator system as defined in claim 2, wherein the dilator defines a shoulder proximal of the dilator head adjacent to which a distal end of the catheter is positioned for insertion into the body.

4. The dilator system as defined in claim 2, wherein the distal portion of the catheter includes a relatively soft atraumatic tip.

5. The dilator system as defined in claim 1, wherein the swellable material includes chemically enhanced polyurethane and polyethylene oxide.

6. The dilator system as defined in claim 1, wherein the swellable material includes a hydratable material.

7. The dilator system as defined in claim 1, wherein the dilator head includes a relatively round cross section.

8. The dilator system as defined in claim 1, wherein the swellable material includes a heat-activated swelling material.

9. The dilator system as defined in claim 1, wherein the dilator defines slits or slots in a wall of the dilator to enable hydration of portions of the catheter that reside outside of the patient.

10. A dilator system for insertion of an elongate device into a body of a patient, comprising:
    an elongate device including a lumen initially defining a first inner diameter, the elongate device including a heat-activated swelling material that swells after insertion into the body in response to heat; and
    a dilator including an elongate body initially disposed in the elongate device lumen and a tapered head extending from a distal end of the elongate device lumen, the dilator head defining an outer diameter substantially equal to or larger than the first inner diameter of the elongate device lumen, the dilator defining a guidewire lumen for passage therethrough of a guidewire, wherein after insertion of the dilator head and a distal portion of the elongate device into the body at least the distal portion of the elongate device swells such that the lumen defines a second inner diameter larger than the outer diameter of the dilator head that enables the dilator to be proximally removed from the body via the elongate device lumen defining the second diameter.

11. The dilator system as defined in claim 10, wherein the elongate device is a catheter.

12. The dilator system as defined in claim 11, wherein the dilator defines a shoulder proximal of the dilator head adjacent to which a distal end of the catheter is positioned for insertion into the body.

13. The dilator system as defined in claim 11, wherein the distal portion of the catheter includes a relatively soft atraumatic tip.

14. The dilator system as defined in claim 11, wherein the dilator head defines a conical shape.

15. A method for inserting a catheter into a body of a patient, the method comprising:
    providing a catheter including a lumen initially defining a first inner diameter, the catheter including a swellable material that swells after insertion into the body;
    positioning a dilator within the catheter lumen, the dilator including an elongate body and a tapered head, the dilator defining a guidewire lumen for passage therethrough of a guidewire, the dilator head defining an outer diameter larger than the first inner diameter of the catheter, the dilator head extending from a distal end of the catheter;
    inserting the dilator head and at least a distal portion of the catheter into the patient body such that the distal portion of the catheter swells and the lumen increases to define a second inner diameter larger than the outer diameter of the dilator head; and
    removing the dilator proximally from the patient body via the lumen of the catheter defining the second inner diameter.

16. The method for inserting as defined in claim 15, wherein inserting the dilator further comprises inserting the dilator into the catheter until the distal end of the catheter is adjacent to a shoulder defined by the dilator head.

* * * * *